US012599366B2

(12) United States Patent
Wen

(10) Patent No.: US 12,599,366 B2
(45) Date of Patent: Apr. 14, 2026

(54) ULTRASOUND IMAGING DEVICE AND METHOD FOR FAST SETUP OF AUTOMATED WORKFLOW THEREOF

(71) Applicant: SHENZHEN MINDRAY BIO-MEDICAL ELECTRONICS CO., LTD., Shenzhen (CN)

(72) Inventor: Bo Wen, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 703 days.

(21) Appl. No.: 17/849,521

(22) Filed: Jun. 24, 2022

(65) Prior Publication Data

US 2023/0132927 A1 May 4, 2023

Related U.S. Application Data

(63) Continuation of application No. PCT/CN2019/129345, filed on Dec. 27, 2019.

(51) Int. Cl.
*A61B 8/00* (2006.01)

(52) U.S. Cl.
CPC ............. *A61B 8/463* (2013.01); *A61B 8/467* (2013.01); *A61B 8/5207* (2013.01)

(58) Field of Classification Search
None
See application file for complete search history.

(56) References Cited

U.S. PATENT DOCUMENTS

| | | | | |
|---|---|---|---|---|
| 2011/0054266 A1* | 3/2011 | Dinino | ................ | G01S 7/52074 |
| | | | | 600/300 |
| 2014/0348401 A1* | 11/2014 | Xu | ......................... | G16H 30/20 |
| | | | | 382/128 |
| 2015/0374344 A1 | 12/2015 | Koide et al. | | |
| 2017/0007161 A1 | 1/2017 | Zou et al. | | |
| 2019/0290932 A1* | 9/2019 | Nioutsikou | .......... | G01R 33/546 |

FOREIGN PATENT DOCUMENTS

| | | |
|---|---|---|
| CN | 105555198 A | 5/2016 |
| CN | 106691504 A | 5/2017 |
| CN | 107569257 A | 1/2018 |
| CN | 109567860 A | 4/2019 |
| JP | 2016-096923 A | 5/2016 |

OTHER PUBLICATIONS

PCT International Search Report and the Written Opinion mailed Oct. 12, 2020, issued in related International Application No. PCT/CN2019/129345, with partial English translation (10 pages).

* cited by examiner

*Primary Examiner* — Michael J Carey
*Assistant Examiner* — Marjan Saboktakin
(74) *Attorney, Agent, or Firm* — Sheppard Mullin Richter & Hampton LLP

(57) ABSTRACT

Disclosed are a method for quickly creating a scanning protocol, and an ultrasonic imaging apparatus using the method. According to the apparatus and the method, a user's scanning operation is recorded to obtain a to-be-examined target section and a setting parameter of the to-be-examined target section, and a target scanning protocol is generated accordingly. In this way, the user only needs to do a scanning operation the user is familiar with, and the target scanning protocol is created in a simple, rapid and efficient manner.

19 Claims, 2 Drawing Sheets

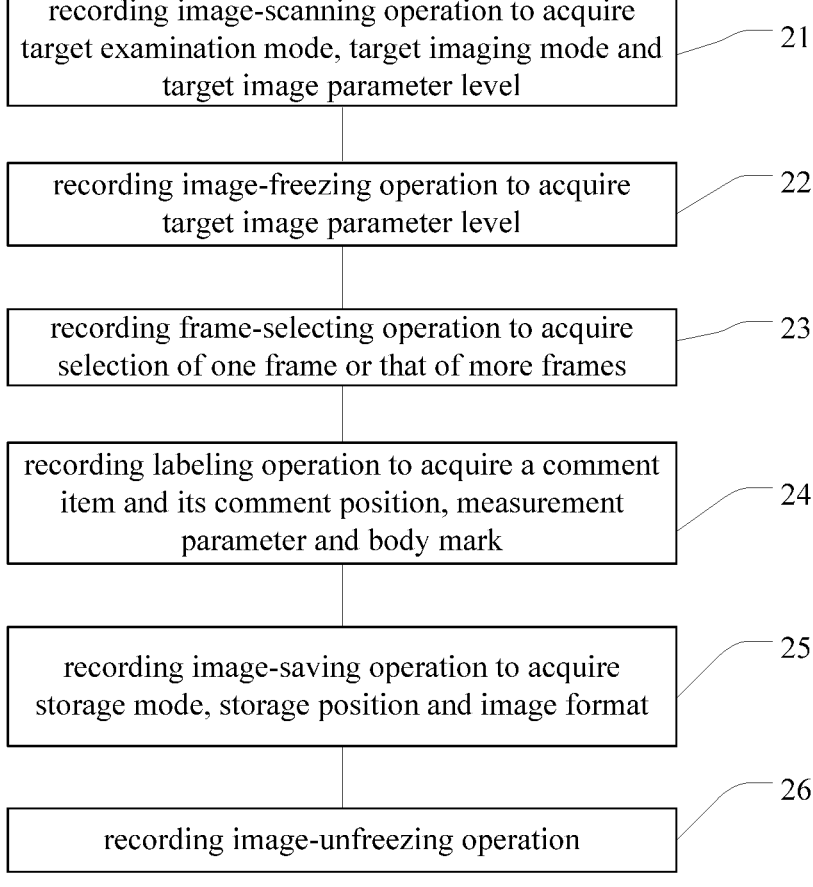

recording image-scanning operation to acquire
target examination mode, target imaging mode and
target image parameter level                          21 recording image-freezing operation to acquire
target image parameter level                          22 recording frame-selecting operation to acquire
selection of one frame or that of more frames          23 recording labeling operation to acquire a comment
item and its comment position, measurement
parameter and body mark                                24 recording image-saving operation to acquire
storage mode, storage position and image format        25 recording image-unfreezing operation                   26

FIG. 3

ULTRASOUND IMAGING DEVICE AND METHOD FOR FAST SETUP OF AUTOMATED WORKFLOW THEREOF

CROSS-REFERENCE TO RELATED APPLICATIONS

This application is a Continuation Application of International Patent Application No. PCT/CN2019/129345 filed with the China National Intellectual Property Administration (CNIPA) on Dec. 27, 2019. The entire content of the above-referenced application is incorporated herein by reference.

TECHNICAL FIELD

The present disclosure relates to medical devices, in particular to ultrasonic imaging apparatus and methods for rapidly configuring ultrasonic automatic workflow.

BACKGROUND OF THE INVENTION

A scanning protocol for ultrasonic automatic workflow is a template protocol that may be designed based on basic operation flows of ultrasonic examination to adapt to a specific application and include at least one to-be-examined section and a setting parameter thereof. The scanning protocol is configured for guiding users to scan various sections of biological tissues, each section configuring with a corresponding setting parameter. It may provide users with the convenience of operation, ensure the standardization and integrity of ultrasonic examination procedure, and prevent missing section(s) and quickly obtain ultrasonic image(s) of each section. However, there are currently several following reasons why doctors want to use the scanning protocol for automatic workflow but they are not comfortable with it.

A user-defined scanning protocol provided by an ultrasonic device manufacturer is complicated in configuration, challenging an operator of the ultrasonic device. It may be acceptable when only a small change to an original scanning protocol is made by doctors; but when there needs to make multiple changes to the protocol or customize a new scanning protocol, a resulted workload is considerable. That is because at present a new scanning protocol is created by configuring not only the combination and sequence of all to-be-examined sections, but also corresponding parameters for each section in the scanning protocol. Further, doctors who usually have less contact with professional software are unfamiliar with control operation and function support provided by the device, resulting in low efficiency in customizing the scanning protocol. It is therefore difficult for the doctors to create a satisfactory scanning protocol by themselves making things out of nothing.

SUMMARY OF THE INVENTION

The present disclosure mainly provides methods for rapidly creating a scanning protocol and an ultrasonic imaging apparatus adopting the methods so as to improve the efficiency of doctors in creating scanning protocols.

According to a first aspect, provided in an embodiment is a method for quickly creating a scanning protocol that comprises at least one to-be-examined section and a setting parameter thereof, comprising:

receiving an instruction to start recording;

in response to the instruction to start recording, displaying a scanning interface, recording a scanning operation performed by a user based on the scanning interface to acquire at least one to-be-examined target section and a setting parameter of the at least one to-be-examined target section; and generating a target scanning protocol containing the at least one to-be-examined target section and the setting parameter of the at least one to-be-examined target section.

According to a second aspect, provided in an embodiment is a method for quickly creating a scanning protocol that comprises at least one to-be-examined section and a setting parameter thereof, comprising:

receiving an instruction to start recording;

in response to the instruction to start recording, controlling an ultrasonic probe to transmit an ultrasonic wave to a target tissue and receive an ultrasonic echo from the target tissue to acquire an ultrasonic echo signal;

acquiring an ultrasonic image based on the ultrasonic echo signal and displaying a scanning interface;

recording a scanning operation performed by a user based on the scanning interface to acquire at least one to-be-examined target section and a setting parameter of the at least one to-be-examined target section; and generating a target scanning protocol containing the at least one to-be-examined target section and the setting parameter of the at least one to-be-examined target section.

According to a third aspect, provided in an embodiment is a method for quickly creating a scanning protocol that comprises at least one to-be-examined section and a setting parameter thereof, comprising:

receiving an instruction to start ultrasonic automatic workflow, and in response to the instruction to start ultrasonic automatic workflow, displaying at least one scanning protocol for a user to select, the scanning protocol comprising at least one to-be-examined section;

displaying a scanning interface of the to-be-examined section of the scanning protocol in response to an instruction to select scanning protocol; recording a scanning operation performed by the user based on the scanning interface in response to an instruction to start recording to acquire at least one to-be-examined target section and a setting parameter of the at least one to-be-examined target section; and generating a target scanning protocol containing the at least one to-be-examined target section and the setting parameter of the at least one to-be-examined target section.

According to a fourth aspect, provided in an embodiment is a method for quickly creating a scanning protocol that comprises at least one to-be-examined section and a setting parameter thereof, comprising:

receiving an instruction to start ultrasonic automatic workflow, and in response to the instruction to start ultrasonic automatic workflow, displaying at least one scanning protocol for a user to select, the scanning protocol comprising at least one to-be-examined section;

in response to an instruction to select scanning protocol, controlling an ultrasonic probe to transmit an ultrasonic wave to a target tissue and receive an ultrasonic echo from the target tissue to acquiring an ultrasonic echo signal;

acquiring an ultrasonic image based on the ultrasonic echo signal and displaying a scanning interface of the to-be-examined section of the scanning protocol;

recording a scanning operation performed by the user based on the scanning interface in response to an instruction to start recording to acquire at least one to-be-examined target section and a setting parameter of the at least one to-be-examined target section; and generating a target scanning protocol containing the at least one to-be-examined target section and the setting parameter of the at least one to-be-examined target section.

According to a fifth aspect, provided in an embodiment is an ultrasonic imaging apparatus, comprising:

an ultrasonic probe configured for transmitting an ultrasonic wave to a region of interest within a biological tissue and receiving an echo of the ultrasonic wave;

a transmitting/receiving control circuit configured for controlling the ultrasonic probe to transmit the ultrasonic wave to the region of interest and receive the echo of the ultrasonic wave to acquire an ultrasonic echo signal;

a human-machine interactive unit configured for receiving an input by a user and outputting visualization information; and a processor configured for: acquiring an ultrasonic image based on the ultrasonic echo signal; receiving an instruction to start recording via the human-machine interactive unit; in response to the instruction to start recording, displaying a scanning interface via the human-machine interactive unit, recording a scanning operation performed by the user based on the scanning interface to acquire at least one to-be-examined target section and a setting parameter of the at least one to-be-examined target section; and generating a target scanning protocol containing the at least one to-be-examined target section and the setting parameter of the at least one to-be-examined target section.

According to a sixth aspect, provided in an embodiment is an ultrasonic imaging apparatus, comprising:

an ultrasonic probe configured for transmitting an ultrasonic wave to a region of interest within a biological tissue and receiving an echo of the ultrasonic wave;

a transmitting/receiving control circuit configured for controlling the ultrasonic probe to transmit the ultrasonic wave to the region of interest and receive the echo of the ultrasonic wave to acquire an ultrasonic echo signal;

a human-machine interactive unit configured for receiving an input by a user and outputting visualization information; and a processor configured for: acquiring an ultrasonic image based on the ultrasonic echo signal; receiving an instruction to start ultrasonic automatic workflow via the human-machine interactive unit, and in response to the instruction to start ultrasonic automatic workflow, displaying at least one scanning protocol for a user to select, the scanning protocol comprising at least one to-be-examined section; displaying a scanning interface of the to-be-examined section of the scanning protocol in response to an instruction to select scanning protocol; recording a scanning operation performed by the user on the scanning interface in response to an instruction to start recording to acquire at least one to-be-examined target section and a setting parameter of the at least one to-be-examined target section; and generating a target scanning protocol containing the at least one to-be-examined target section and the setting parameter of the at least one to-be-examined target section.

According to a seventh aspect, provided in an embodiment is an ultrasonic imaging apparatus comprising: a memory for storing a program; and a processor for executing the program stored in the memory to implement the method mentioned above.

According to an eighth aspect, provided in an embodiment is a computer-readable storage medium having a program that can be executed by a processor to implement the method mentioned above.

According to the ultrasonic imaging apparatus and the methods for quickly creating a scanning protocol mentioned in aforesaid embodiments, a user's scanning operation is recorded to obtain a target to-be-examined section and a setting parameter of the target to-be-examined section, and a target scanning protocol is generated accordingly. In this way, the user only needs to do a scanning operation the user is familiar with, and the target scanning protocol is created in a simple, rapid and efficient manner.

BRIEF DESCRIPTION OF THE DRAWINGS

FIG. 3 is a flowchart of step 2 in FIG. 2.

DETAILED DESCRIPTION

Figure 1:
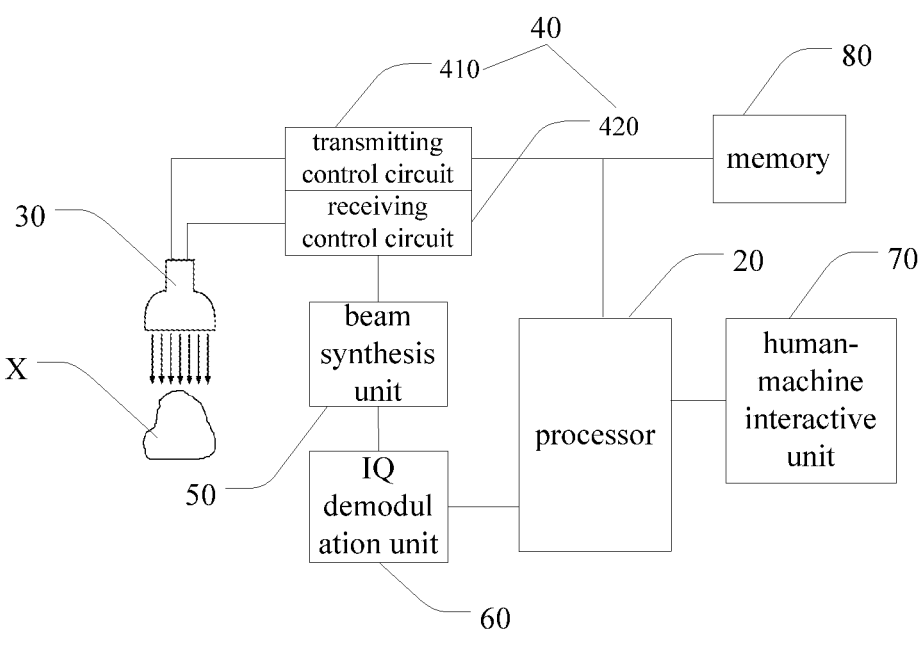
FIG. 1 is a block diagram of an ultrasonic imaging apparatus according to the present disclosure.

The present disclosure will be further described in detail below through specific embodiments with reference to the accompanying drawings. Common or similar elements are referenced with like or identical reference numerals in different embodiments. Many details described in the following embodiments are for better understanding the present disclosure. However, those skilled in the art can realize with minimal effort that some of these features can be omitted in different cases or be replaced by other elements, materials and methods. For clarity some operations related to the present disclosure are not shown or illustrated herein so as to prevent the core from being overwhelmed by excessive descriptions. For those skilled in the art, such operations are not necessary to be explained in detail, and they can fully understand the related operations according to the description in the specification and the general technical knowledge in the art.

In addition, the features, operations or characteristics described in the specification may be combined in any suitable manner to form various embodiments. At the same time, the steps or actions in the described method can also be sequentially changed or adjusted in a manner that can be apparent to those skilled in the art. Therefore, the various sequences in the specification and the drawings are only for the purpose of describing a particular embodiment, and are not intended to be an order of necessity, unless otherwise stated one of the sequences must be followed.

The serial numbers of components herein, such as "first", "second", etc., are only used to distinguish the described objects and do not have any order or technical meaning. The terms "connected", "coupled" and the like here include direct and indirect connections (coupling) unless otherwise specified.

As shown in FIG. 1, an ultrasonic imaging apparatus provided in the present disclosure may include an ultrasonic probe 30, transmitting/receiving control circuits 40, a beam synthesis unit 50, an IQ demodulation unit 60, a processor 20, a human-machine interactive unit 70 and a memory 80.

The ultrasonic probe 30 may include a transducer (not shown in the figure) composed of a plurality of elements arranged in an array. The plurality of elements may be arranged in a row to form a linear array, or in a two-dimensional matrix to form an area array, or in a convex array. The transducer may be configured to transmit ultrasonic waves based on excited electrical signals, or convert received ultrasonic echoes into electrical signals. Accordingly, each element may be configured to mutually convert electrical pulse signals and ultrasonic waves, realizing transmitting ultrasonic waves to target tissues to be examined (e.g. a region of interest within organs, tissues, blood vessels, fetuses and other biological tissues of human or animal) and/or receiving ultrasonic echoes reflected by the tissues. During ultrasonic examination, it is possible to, via a transmitting control circuit 410 and a receiving control circuit 420, control which elements to transmit ultrasonic waves and which elements to receive ultrasonic echoes, or control the elements to transmit ultrasonic waves and receive ultrasonic echoes in time slots. The elements participating in the transmission of the ultrasonic waves may simultaneously be excited by electrical signals to transmit the ultrasonic waves at the same time; or, the elements participating in the transmission of the ultrasonic waves may also be excited by several electrical signals with a certain time interval to continuously transmit the ultrasonic waves with a certain time interval.

The elements using for example piezoelectric crystals may convert electrical signals into ultrasonic signals according to a transmission sequence transmitted by the transmitting control circuit 410. The ultrasonic signals may, depending on actual purpose, include one or more scanning pulses, one or more reference pulses, one or more drive pulses, and/or one or more Doppler pulses. The ultrasonic signals may include focused waves and plane waves according to wave morphology.

The ultrasonic probe 30 may be moved by a user to an appropriate position and angle to transmit an ultrasonic wave to a measured tissue X and receive an ultrasonic echo from the measured tissue X to output an ultrasonic echo signal. The ultrasonic echo signal is a channel (formed by the elements configured for receiving) analog electrical signal carried amplitude information, frequency information and time information.

The transmitting control circuit 410 may be configured to generate a transmission sequence based on the control of the processor 20. The transmission sequence may be configured to control all or part of the plurality of the elements to transmit ultrasonic waves to a target tissue; and a parameter involved in the transmission sequence (transmission sequence parameter for short) may include the position of the elements configured for transmitting, the number of the elements, and an ultrasonic beam transmitting parameter (such as amplitude, frequency, transmission times, transmission interval, transmission angle, wave type, focusing position, etc.). In some cases, the transmitting control circuit 410 may also be configured to perform phase delay on the transmitted ultrasonic beam, so that ultrasonic waves can be transmitted at different times by different transmitting elements and each transmitted beam can focus in a predetermined region of interest. The transmission sequence parameter under different working modes, such as B imaging mode, C imaging mode and D imaging mode (Doppler mode), may be different; in this respect, after receiving the echo signal via the receiving control circuit 420 and performing the received signal with subsequent unit(s) and corresponding algorithm(s), a B image reflecting tissue anatomical structure, a C image reflecting tissue anatomical structure and blood flow information, and a D image reflecting Doppler spectrum image may be generated.

The receiving control circuit 420 may be configured to receive and process the ultrasonic echo signal from the ultrasonic probe. The receiving control circuit 420 may comprise one or more amplifiers, analog-to-digital converters (ADC), and the like. The amplifier(s) may be used to amplify the received echo signal after appropriate gain compensation. The ADC(s) may be used to sample an analog echo signal at a predetermined time interval to convert it into a digital signal. The digitized echo signal may still retain the amplitude information, the frequency information and the phase information. The data received from the receiving control circuit 420 may be outputted to the beam synthesis unit 50 for processing, or to the memory 80 for storage.

The beam synthesis unit 50 connected with the receiving control circuit 420 in a signal-connection manner may be used to perform beam synthesis on the echo signal, including corresponding time delaying and weighted summing. Because the distances between ultrasonic receiving points in the measured tissue and the receiving elements may be different, there may exist delay difference in the channel data outputted by different receiving elements corresponding to the same receiving point; accordingly, there may be a need to perform a time-delay processing for phase alignment, and perform weighted summation on the different channel data of the same receiving point to obtain ultrasonic image data after beam synthesis. The ultrasonic image data outputted by the beam synthesis unit 50 may also referred to as radio frequency data (RF data). The beam synthesis unit 50 may transmit the RF data to the IQ demodulation unit 60; however, in some embodiment, it may also output the RF data to the memory for caching or storage, or directly output the RF data to the processor 20 for image processing.

The beam synthesis unit 50 may implement the above functions in the way of hardware, firmware or software. For example, the beam synthesis unit 50 may include a central controller circuit (CPU), one or more microprocessor or any other electronic component(s) for processing input data according to specific logic instruction(s); and when the beam synthesis unit 50 is implemented in software, it may execute the instruction(s) stored on tangible and non-transient computer-readable media (e.g. memory) for beam synthesis using any appropriate beam synthesis method.

The IQ demodulation unit 60 may remove signal carrier through IQ demodulation, extract tissue structure information contained in the signal, and perform filtering to remove noise. The signal obtained at this time may be referred to as a baseband signal (IQ data pair). The IQ demodulation unit 60 may output the IQ data pair to the processor for image processing.

In some embodiments, the IQ demodulation unit 60 may also transmit the IQ data pair to the memory 80 for caching or storage, such that the processor 20 can read the data from the memory 80 for subsequent image processing.

Similarly, the IQ demodulation unit 60 may implement the above functions in the way of hardware, firmware or software. In some embodiments, the IQ demodulation unit 60 may also be integrated in a chip with the beam synthesis unit 50.

The processor 20 may be configured as a central controller circuit (CPU), one or more microprocessors, a graphical controller circuit (GPU) or any other electronic component capable of processing input data according to specific logic instructions. It may perform control on a peripheral electronic component in response to an input or predetermined instruction, perform data reading and/or saving on the memory 80, or process the input data by performing the program(s) in the memory 80. For example, the processor may perform one or more processing operations on the acquired ultrasonic data according to one or more working modes. The processing operations may include, but not limit to, adjusting or confining the form of ultrasonic waves transmitted by the ultrasonic probe 30, generating various image frames for display on a display of the subsequent human-machine interactive unit, or adapting or limiting the content and form displayed on the display, or configuring one or more image display settings (e.g. ultrasonic images, interface components, positioning regions of interest) displayed on the display.

When receiving the echo signal, the acquired ultrasonic data may be processed in real time by the processor 20 during scanning or treatment, or it may store temporarily in the memory 80 and processed in a quasi-real time manner in online or offline operations.

In the embodiment, the processor 20 may control the operation of the transmitting control circuit 410 and the receiving control circuit 420, for example, it may control the transmitting control circuit 410 and the receiving control circuit 420 to operate alternately or simultaneously. The processor 20 may also determine an appropriate working mode in response to a user's selection or program setting to form a transmission sequence corresponding to a current working mode, and send the transmission sequence to the transmitting control circuit 410 so as to control the ultrasonic probe 30 to transmit ultrasonic waves in an appropriate transmission sequence adopted by the transmitting control circuit 410.

The processor 20 may also configured to process the ultrasonic data to generate a grayscale image with varying signal strength within a scanning range. The grayscale image referred to as B image may reflect the anatomical structure inside the tissue. The processor 20 may output the B image to the display of the human-machine interactive unit 70 for display.

The human-machine interactive unit 70 may be configured for human-machine interaction, that is, for receiving a user's input and outputting visualization information. The user's input may be received by a keyboard, an operation button, a mouse, a trackball, etc., or a touch screen integrated with the display. The visualization information may be outputted by the display.

An available ultrasonic imaging apparatus may usually provide with a plurality of existing scanning protocols for users to select and operate. The scanning protocol may include at least one to-be-examined section and a setting parameter thereof. For example, A scanning protocol for fetal brain examination may include to-be-examined sections including a transverse section of thalamus, a section of lateral ventricle, and a transverse section of the cerebellum. When a user needs to obtain ultrasonic images of these sections through ultrasonic scanning, there is actually a standard scanning process. That is to say, the scanning protocol is a template protocol that may be designed based on basic operation flows of ultrasonic examination and be adapted to a specific application, which may provide fast and convenient operation for an ultrasonic scanning operator, guaranteeing a standard and integrated examination process and preventing omission of section(s) and measurement. After the scanning protocol is activated, the ultrasonic imaging apparatus may guide the user to execute the standard scanning process through a display interface, so that an image of the to-be-examined section and measurement data thereof may be obtained. The setting parameter may refer to a parameter for setting the standard scanning process of the section(s).

For an existing ultrasonic imaging apparatus, it is very complicated to configure parameter(s) on a system setting interface due to a large variety of functions provided by the apparatus. In particular, users usually use an existing scanning protocol rather than a user-defined scanning protocol to perform scanning operations, so they may be unfamiliar with the operation of customizing a scanning protocol; accordingly, the workload thereof may be very heavy for the users when there is a need to customizing a scanning protocol.

With the method for quickly creating a scanning protocol provided in the present disclosure, a scanning process of a normal examination by a user is recorded to extract a target to-be-examined section and a setting parameter of the target to-be-examined section, accordingly a new scanning protocol is generated based thereon. Different from the existing scanning protocols in the system, the new scanning protocol is user-defined. There is no need to make complicated settings in an exclusive process setting page, nor recalling and conceiving during setting in the method disclosed herein; instead, it only requires to perform only one normally complete scanning operation. The scanning operation is the most familiar to users, therefore the method for quickly creating a scanning protocol is very easy for users to get started, with simple, convenient and fast operation. The method is illustrated in detail in the following embodiments.

Figure 2:
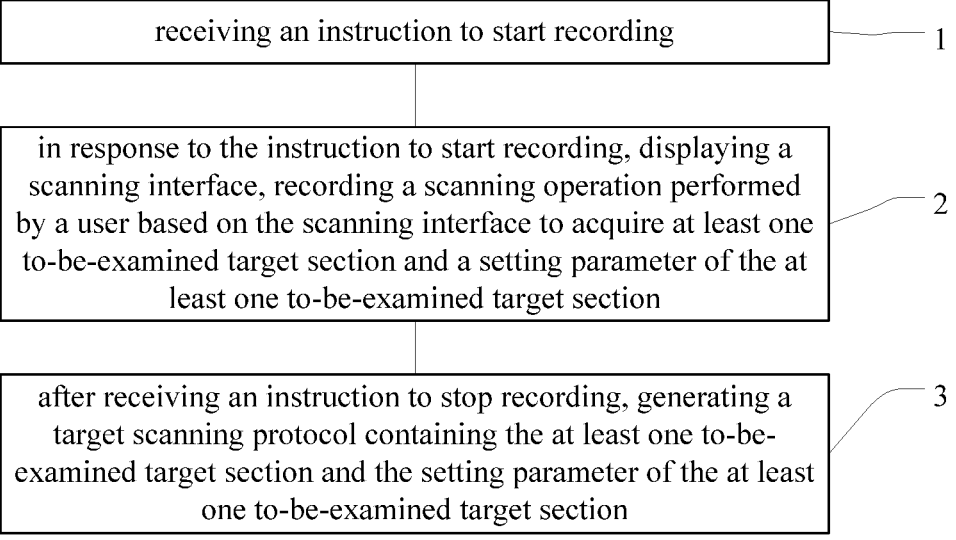
FIG. 2 is a flowchart of a method for quickly creating a scanning protocol according to the present disclosure.

Based on the ultrasonic imaging apparatus shown in FIG. 1, a flowchart of quickly creating a scanning protocol is shown in FIG. 2, including the following steps:

Step 1: receiving an instruction to start recording via the human-machine interactive unit 70 by the processor 20. The instruction may be triggered by a specific button in the human-machine interactive unit 70, or by a cursor click in some display interfaces. For example, an instruction to start ultrasonic automatic workflow may be sent by the user via the human-machine interactive unit 70. The ultrasonic automatic workflow may be a workflow that guides the user to conduct ultrasonic scanning, which may be equivalent to a collection of various contents to be scanned. The processor 20 may receive the instruction to start the ultrasonic automatic workflow via the human-machine interactive unit 70, and then in response to the instruction to start the ultrasonic automatic workflow, display an icon for triggering the instruction to start recording and at least one existing scanning protocol for the user to select via the human-machine interactive unit 70, wherein the existing scanning protocol may include at least one existing to-be-examined section. The existing scanning protocol may be a scanning protocol that come with an ultrasonic imaging apparatus with it is delivered. The user can perform a regular scanning operation by selecting the existing scanning protocol, or record the scanning operation by selecting the icon for triggering the instruction to start recording to quickly creating a scanning protocol. When the icon is selected, the instruction to start recording may be sent out. Of course, the access to quickly create a scanning protocol is not limited to this, for example it may include setting a shortcut key which may be a specific button or be displayed normally on some display interfaces; and accordingly, the click of the shortcut key by the user may trigger the instruction to start recording.

Step 2: in response to the instruction to start recording, displaying a scanning interface via the display and recording the scanning operation performed by the user based on the scanning interface by the processor 20 to acquire at least one target to-be-examined section and a setting parameter of the at least one target to-be-examined section. The ultrasonic probe may enter a working state before or after recording. By means of exciting the ultrasonic probe to transmit an ultrasonic wave to a target tissue and receive an ultrasonic echo from the target tissue to obtain an ultrasonic echo signal, the ultrasonic probe may enter the working state, so that an ultrasonic image may be acquired based on the ultrasonic echo signal, and a corresponding scanning interface may be displayed. The scanning operation may include: at least one of: image-scanning operation, image-freezing operation, frame-selecting operation, labeling operation, image-saving operation and image-unfreezing operation; and the labeling operation may include at least one of: adding a body mark, commenting, and measuring. In order to illustrate the solution of the present disclosure in more detail, the scanning operation including all the above operations is taken as an example in the present embodiment. As shown in FIG. 3, step 2 may specifically include:

Step 21: acquiring a current to-be-examined target section by the processor 20. The processor 20 may create a to-be-examined target section corresponding to a target scanning operation by default after receiving the instruction to start recording, or create a to-be-examined target section by default whenever any-one scanning operation is performed by the user; and after creating the to-be-examined target section, all current scanning operation(s) may belong to the scanning operation of the to-be-examined target section until a next to-be-examined target section is created. The name of the to-be-examined target section may be a default name (such as a blank name for subsequent editing), or it may be obtained after subsequent operation.

Based on the user's operation, the processor 20 may control the ultrasonic probe 30 to perform ultrasonic imaging process and record the image-scanning operation during the ultrasonic imaging process. For example, examination mode, image mode and image parameter level may be provided on a display interface, or they may be provided on the display interface based on the user's operation for the user to select. The ultrasonic imaging process may refer to scanning image(s) by the user (such as a doctor) using the ultrasonic probe to obtain ultrasonic image(s) of tissue(s) and organ(s) to be scanned. For example, the ultrasonic probe may be excited to transmit the ultrasonic wave to the target tissue and receive the ultrasonic echo from the target tissue so as to obtain the ultrasonic echo signal, and the ultrasonic image may be acquired based on the ultrasonic echo signal. During real-time ultrasonic imaging, the examination mode and the image mode may be first set by the doctor; wherein the image mode may include but not limit to B image mode, C image mode and D image mode (Doppler mode), and the examination mode may include but not limit to abdomen in adults, abdomen in children, middle pregnancy, fetal heart, carotid artery and thyroid gland. The processor 20 may take the examination mode and the image mode used last time as target examination mode and target image mode, record the target examination mode and the target image mode adopted in the image-scanning operation for the current to-be-examined target section, and take the target examination mode and the target image mode as the setting parameter of the current to-be-examined target section. The processor 20 may, when executing the target scanning protocol subsequently, control the ultrasonic probe to automatically switch to the target examination mode and the target image mode based on the setting parameter (the target examination mode and the target image mode) corresponding to the scanned section, which is very convenient without selection by the doctors.

Various image parameters (depth, gain, frequency, beam direction, contrast, etc.) may be adjusted by doctors in real-time scanning state and image freezing state to obtain effects that are conducive to diagnosis. Different patients (such as with different body shapes, ages, etc.) may need to set different image parameter levels. When the target scanning protocol that a doctor needs to generate is a general protocol, it may be generally unnecessary to record the image parameter level. That is because it may still need to be adjusted frequently due to various patients in actual examination, and a set image parameter level is not convenient. When the target scanning protocol that a doctor needs to generate is for a certain class of patients (such as children or obese patients, etc.), the image parameter can reflect consistent directivity to a certain extent, then the image parameter level may be recorded during recording. For example, by providing an option for doctors to choose whether to record the image parameter level when configuring a recording protocol via a setting interface, a doctor may set up in advance before recording. Assuming that a doctor chooses to record the image parameter level, the processor 20 may record the image parameter level as the setting parameter. Since there may exist an intermediate regulating process (e.g. there is level 3 when adjusting level 2 to level 4) during the selection of the image parameter level by the doctor, the processor 20 may take the image parameter level last used in the real-time scanning state as a target image parameter level, and take the target image parameter level in the real-time scanning state as the setting parameter of the current to-be-examined target section. In a subsequently execution of the target scanning protocol, under the real-time scanning state, the processor 20 may automatically load the target image parameter level in the real-time scanning state.

Step 22: freezing the ultrasonic image by a doctor after finishing real-time scanning of the ultrasonic image. For example, an image-freezing instruction may be inputted by a doctor via the human-machine interactive unit, then the ultrasonic image obtained by real-time scanning may be frozen. It may be kept in an image frozen state until it is unfrozen. Similarly, the image parameter level of the frozen ultrasonic image may be adjusted by the doctor, accordingly, the processor 20 may take the image parameter level last used in the image frozen state as the target image parameter level, and take the target image parameter level in the image frozen state as the setting parameter of the current to-be-examined target section. In a subsequently execution of the target scanning protocol, under the image frozen state, the processor 20 may automatically load the target image parameter level in the image frozen state.

The target image parameter level in the real-time scanning state and that in the image frozen state may both be recorded in the present embodiment; and of course, in some embodiments, it is also possible to record only the target image parameter level in the image frozen state.

Step 23: providing a corresponding human-machine interactive interface on the display interface of the display for doctors to select frame(s) after the ultrasonic image is frozen. For example, one or more frames of ultrasonic image(s) that may be the most appropriate may be selected from a plurality of frozen ultrasonic images by sliding a playback lever backward by a doctor (i.e. the frame-selecting operation) for a subsequent labeling operation. The processor 20 may record whether one frame or multiple frames is selected by the doctor and take the recorded result as the setting parameter of the current to-be-examined target section. In a subsequently execution of the target scanning protocol, the processor 20 may correspondingly prompt the user to choose one frame or multiple frames via the display interface after the ultrasonic image is frozen.

Step 24: performing the labeling operation which includes at least one of adding a body mark, commenting and measuring after one or more frames of ultrasonic images are selected by the doctor. The labeling operation including all the three is taken as an example for illustrating the present embodiment. After a comment item is added at a certain position of the selected ultrasonic image by the doctor, the processor 20 may record the added comment item and the comment position thereof, and take the comment item and the comment position thereof as the setting parameter of the current to-be-examined target section. The comment item may include a section name, a section state (such as whether it is pressed, etc.). In conventional ultrasonic examination, there may be one or more comments for each section, or no comments may be required. What must or preferably to be commented may be completed at one time by a doctor as needed when recording a protocol, which may be recorded by the processor 20. In a subsequently execution of the target scanning protocol, the processor 20 may, after one or more frames of ultrasonic images are selected, display the comment item at the comment position of the selected ultrasonic image via the display interface to prompt the doctor. Of course, in other embodiments, the processor 20 may also record only the comment item or the comment position as the setting parameter; under such circumstances, in a subsequently execution of the target scanning protocol, the comment item of the setting parameter may be displayed and the comment position may be selected by the doctor, or the comment position of the setting parameter may be displayed and the comment item may be selected by the doctor.

Measurement may be performed on one or more frames of ultrasonic images selected by the doctor, and various measurement parameters including a measurement item and a measurement method may be shown on the display interface for doctors to choose. The measurement item may include but not limit to carotid spectrum measurement, fetal head circumference measurement and gynecological cervical length measurement; and the measurement method may include but not limit to PS, two-point method, tracing method, spline method, automatic method, ellipse method, reticle method and automatic method. The processor 20 may record the measurement parameter that is added by a doctor, and take the added measurement parameter as the setting parameter of the current to-be-examined target section. In a subsequently execution of the target scanning protocol, after one or more frames of ultrasonic images are selected by the doctor, the processor 20 may prompt the doctor on the display interface to measure according to the measurement item of the setting parameter, and the measurement method of the setting parameter may need to be used when measuring. Junior doctors may often be prone to forget performing measurement, and may be unsure about various measurement methods. The method for quickly creating a scanning protocol disclosed herein may be operated by senior doctors, and the acquired target scanning protocol may reflect the working flow of ultrasonic examination performed by the senior doctors, which is more standardized and detailed than that operated by junior doctors themselves. Subsequently, the junior doctors may use the target scanning protocol to conduct better examination and practice operation, which is convenient to improve their working efficiency and quality.

A body mark may be added to one or more frames of ultrasonic images selected by doctors; and the processor 20 may record the added body mark and take the body mark as the setting parameter of the current to-be-examined target section. For the section in a standardized examination process, there may be generally a fixed posture of patients and a stationary position and direction of probe placement; in this respect, after configuring during recording, in a subsequently execution of the target scanning protocol, the processor 20 may automatically load the body mark of the setting parameter, without the need for doctors to set.

Step 25: saving the ultrasonic image after performing adding body mark, comment and measurement on the ultrasonic image selected by doctors, that is, the image-saving operation. The instruction to save image may be transmitted by the doctor via the human-machine interactive unit, and then a plurality of storage modes may be shown on the display interface for the doctor to select. The storage modes may include: storing a single frame of ultrasonic image from frozen ultrasonic image(s), forward-storing a clip of ultrasonic images, backward-storing a clip of ultrasonic images, or storing static ultrasonic image(s). Storing a single frame of ultrasonic image from frozen ultrasonic image(s) may for example refer to storing a frame of ultrasonic image that has been selected before being stored. For forward-storing or backward a clip of ultrasonic images, it should be noted that "forward-storing" may refer to forward storage along a timeline, that is, to store a clip of images in the direction in which time has passed (i.e. those has been scanned and stored in an image memory); and "backward-storing" may refer to backward storage along the timeline, that is, to store a clip of images in the direction of future time (i.e. those not scanned). The ultrasonic images in the aforesaid storage modes may be editable, that is, they may be conducted with an added body mark, comment or measurement. Storing static ultrasonic image(s) may refer to storing an ultrasonic image in an non-editable image format. The processor 20 may, after receiving the instruction to save image, record the storage mode selected by the user and take the selected storage mode as the setting parameter of the current to-be-examined target section.

After the storage mode is selected, a storage position and an image format may be selected by the doctor; and the processor 20 may record the storage position of the saved ultrasonic image and take the storage position as the setting parameter of the current to-be-examined target section, and record the image format of the saved ultrasonic image and take the image format as the setting parameter of the current to-be-examined target section. The storage position may be either stored locally (in the ultrasonic imaging apparatus) or in a sever, which may be selected by doctors. In a subsequently execution of the target scanning protocol, there may be unnecessary for the user to configure the storage position and image format again, and the processor 20 may perform, by default, storage in the storage position of the setting parameter and take the image format as the image format of the setting parameter, improving the operation efficiency.

The saved ultrasonic image may need to be printed by the doctor; and the processor 20 may, after receiving an instruction to print image, record a print setting and take the print setting as the setting parameter of the current to-be-examined target section.

There may be a need to set a guide image for the doctor. The display interface showing a plurality of guide images may be called up by the operation of the doctor, and one guide image may be selected therefrom by the doctor. The processor 20 may, after receiving an instruction to select guide image, take the selected guide image as the setting parameter of the current to-be-examined target section. A more automated approach may also definitely be adopted; in this respect, the processor 20 may extract an anatomical structure contour from the ultrasonic image selected in the scanning operation (e.g. from one or more frames of ultrasonic images selected by doctors), search the guide image most similar to the anatomical structure contour from a plurality of pre-stored guide images, and take the searched guide image as the setting parameter of the current to-be-examined target section. In a subsequently execution of the target scanning protocol, the processor 20 may show the guide image on the display interface so as to guide the doctor to conduct ultrasonic scanning on the to-be-examined target section.

Step 26: unfreezing the image. It may usually mean that the current frozen image is no longer needed or the current scanning is finished and a new scanning is about to start. The processor 20 may, after receiving an instruction to unfreeze image, judge whether the ultrasonic image has been saved in the current to-be-examined target section. When the ultrasonic image has been saved, the image may be unfrozen so as to perform scanning and recording on a next to-be-examined target section; and when the ultrasonic images corresponding to the current to-be-examined target section have not been saved, the setting parameter obtained currently may be deleted. For example, when the doctor finds that none of the frozen ultrasonic images can meet requirements, or the doctor may be unsatisfied with the setting parameter obtained in the previous steps, the image may be unsaved and unfrozen, a new image-scanning operation may be performed, and the setting parameter corresponding to the current to-be-examined target section may be automatically deleted.

The operation to examine various sections are similar to some extent in routine clinically ultrasonic examination, including scanning, freezing, frame selection, adding body mark and comment, measurement, image saving and unfreezing, namely steps 21-26. A corresponding instruction may be inputted by the doctor to finish the record of the current to-be-examined target section to perform the record of a next to-be-examined target section; alternatively, the processor 20 may recognize a key operation of the doctor as a basis for ending the record of the current to-be-examined target section. The latter is described in the embodiment. Assuming that the scanning operation performed by a doctor is regarded as a preset key operation, the processor 20 can recognize the scanning operation, and then obtain the setting parameter of the to-be-examined target section according to the records of the scanning operation from the image-scanning operation to the key operation. For example, the saved image may often be a sign of the completion of the examination on the section, which may be used as a diagnostic basis or kept for future check. If the key operation is to save the image, the processor 20 may, after recognizing the image-saving operation by a doctor (see step 25), consider that the examination and record of the current to-be-examined target section have been completed, take the setting parameter obtained in steps 21-25 as the setting parameter of the current to-be-examined target section, and categorize the setting parameter obtained later as the setting parameter of another to-be-examined target section. And when the key operation is the image-unfreezing operation, the setting parameter obtained in steps 21-26 may be determined as the setting parameter of the current to-be-examined target section, and then the image may be unfrozen.

There may exist a plurality of ultrasonic images of to-be-examined target section in the ultrasonic images frozen by a doctor; in this respect, the image-saving operation is preferably chosen as the key operation in the embodiment. A to-be-examined target section and the setting parameter thereof may be acquired after the operations of image selection, labeling and saving performed by the doctor. Since there may be an ultrasonic image of other to-be-examined target section in the frozen images, another to-be-examined target section and the setting parameter thereof may also be acquired after re-performing image selection, labeling and image saving. Until there is no other to-be-examined target section in the frozen ultrasonic image, the image may be unfrozen and a next to-be-examined target section may be scanned and recorded.

The processor 20 may, after receiving the instruction to start recording, prompt the user to set the name of the target scanning protocol on the display interface of the display, and determine the name of the target scanning protocol according to the user's input. Alternately, a preset first name may be adopted as the name of the target scanning protocol. That is to say, when no input about the name of the target scanning protocol is inputted by a doctor during recording, the first name may be used as the name of the target scanning protocol. The first name may be editable for the doctor to change later. The processor may, during the record of the to-be-examined target section, prompt the user to set the name of the to-be-examined target section on the display interface of the display, determine the name of the to-be-examined target section according to the user's input, and take the determined name of the to-be-examined target section as the setting parameter of the current to-be-examined target section. Definitely, a preset second name may be adopted as the name of the to-be-examined target section, and the second name may be taken as the setting parameter of the current to-examined. In other words, when no input about the name of the to-be-examined target section is inputted by the doctor during recording, the second name may be used as the name of the to-be-examined target section. The second name may be editable for the doctor to change later.

The procedure of how to acquire a to-be-examined target section and a setting parameter thereof is described above. Doctors only need to scan according to their own needs; and the processor 20 is capable of record, regardless of the number of the to-be-examined target section and that of the setting parameter thereof. Of course, the to-be-examined target section of the target scanning protocol that may need to be generated by a doctor may not require all of the aforesaid setting parameters. The doctors may conduct operation corresponding to their own needs, that is, steps 21-25 may be executed selectively. Since there may be a plurality of to-be-examined target objects, the processor 20 may, after receiving the instruction to start recording, also prompt the user to set a starting sequence of the plurality of to-be-examined target objects on the display interface of the display, determine the starting sequence of the plurality of to-be-examined target objects according to the user's input, and take the starting sequence of each to-be-examined target section as the setting parameter thereof.

In order to facilitate doctors to acknowledge the process of recording, after receiving the instruction to start recording, the processor 20 may display on the display interface of the display the process of acquiring each to-be-examined target section and the setting parameter thereof in the scanning operation until receiving a stop-recording instruction. For example, a process may be prompted to a doctor by means of the following table:

| record sequence | section | record process |
|---|---|---|
| 1 | name of section 1 | |
| 2 | name of section 2 | + . . . + |
| 3 | name of section 3 | + . . . + |
| . . . | | |

The above table shows not only the record sequence of the plurality of the sections, but also guide charts in the column of section name. Doctors may acknowledge the name of section via corresponding guide chart without checking the text content, which is convenient and fast.

When each to-be-examined target section and the setting parameter thereof are recorded by the doctor, the processor 20 may, after receiving the instruction to start recording, provide operations including copy, retake, delete, insert forward, insert backward, pause/continue on the display interface for the doctor to choose. For example, the following table provides the doctor with corresponding operation access:

| copy | retake | delete | insert forward | insert backward | pause/continue |
|---|---|---|---|---|---|

After receiving the instruction to start recording, the processor 20 may receive an instruction to copy inputted by the user via the human-machine interactive unit, and copy the to-be-examined target section selected by the user so as to acquire another group of setting parameter of the to-be-examined target section. Such copy may be duplicated completely without change, or it may be changed automatically after duplicated. There may be two groups of setting parameters for one to-be-examined target section, such that a plurality of groups of parameters may be sampled during scanning the same target in a subsequently execution of the target scanning protocol. For example, the settings associated with a left limb section may be copied as those associated with a right limb section, and the name and part of the settings may be modified at the same time.

The processor 20 may, after receiving the instruction to start recording, also receive an instruction to retake inputted by the user via the human-machine interactive unit, and delete the setting parameter of the to-be-examined target section selected by the user to regain the setting parameter.

The processor 20 may, after receiving the instruction to start recording, also receive an instruction to delete inputted by the user via the human-machine interactive unit, delete the to-be-examined target section selected by the user, and update the sequence of other target sections to be examined.

The processor 20 may, after receiving the instruction to start recording, also receive an instruction to forward-insert via the human-machine interaction, and insert a new to-be-examined target section before selecting the to-be-examined target section by the user; or it may receive an instruction to backward-insert via the human-machine interactive unit, and insert a new to-be-examined target section after selecting the to-be-examined target section by the user. In this way, it is convenient for the user to adjust the sequence of the target sections to be examined.

The processor 20 may, receiving the instruction to start recording, also receive an instruction to pause recording inputted by the human-machine interactive unit, and pause current recording for the convenience of a doctor to perform other operations. When the doctor may need to continue recording, an instruction to continue recording may be received via the human-machine interactive unit to continue the current recording.

Step 3: generating a target scanning protocol based on the to-be-examined target section and the setting parameter thereof obtained in step 2. The target scanning protocol may include at least one to-be-examined target section and the setting parameter thereof obtained in step 2. Generally, depending on the number of the to-be-examined target section and that of the setting parameter thereof obtained in step 2, there may be corresponding number of the to-be-examined target section and that of the setting parameter thereof in the generated target scanning protocol. The generated target scanning protocol may be generated during recording, or be generated after the processor 20 receives the stop-recording instruction via the human-machine interaction 70. The latter may be taken as an example to illustrate the embodiment. After the scanning operation has been performed on each to-be-examined target section by the doctor, and the stop-recording instruction has been inputted via the human-machine interactive unit 70, the processor 20 may stop recording the scanning operation so as to generate a target scanning protocol that include all the to-be-examined target section and the setting parameters thereof obtained in step 2.

It can be seen that the target scanning protocol generated by the present disclosure is generated according to doctors' personal habits during the scanning operation on a section, making the doctors feel familiar and convenient when operating. Moreover, the generated target scanning protocol conforms to the doctors' habits and minds. In addition, if the operation is performed by an experienced doctor, the generated target scanning protocol is more perfect.

Some ultrasonic examinations may be bilateral limb examinations (e.g. blood vessels, nerves, musculoskeletal examinations, etc.) together with unilateral limb examinations. For doctors, it is obvious that they do not want to repeat the recording of a protocol of bilateral limb after recording protocols of unilateral limb separately; instead, they may want to combine the protocol of left limb with that of right limb to be a protocol of bilateral limb. In this respect, the processor 20 may be configured to, after generating the target scanning protocol, receive an instruction to combine via the human-machine interactive unit and combine two target scanning protocols selected by the user in accordance with the sequence of the two target scanning protocols selected by the user. That is to say, when a doctor chooses two protocols and presses a "combined" button, the processor 20 may, according to the sequence of the target scanning protocols, automatically generate a combined protocol which can be renamed or adjusted or modified by the doctors. The combination is definitely unlimited to two protocol, it can refer to a plurality of protocols which may be combined in accordance with the selected sequence.

The target scanning protocol, like an existing scanning protocol, is a protocol file containing at least one to-be-examined target section and the setting parameter of the at least one to-be-examined target section. When starting the target scanning protocol, doctors may be guided via a human-machine interactive unit to scan which target sections to be examined. Each to-be-examined target section is configured with corresponding setting parameter, so there is no need for doctors to set too many parameters during scanning, further doctors can quickly acquire an image of each to-be-examined target section.

The target scanning protocol, after generated, may be used in the same way as the existing scanning protocol provided by an ultrasonic imaging apparatus. The following briefly describes the process of implementing the target scanning protocol:

Doctors may send an instruction to start ultrasonic automatic workflow via the human-machine interactive unit 70. In response to the instruction to start the ultrasonic automatic workflow, the processor 20 may display on the display interface of the display an icon for triggering the instruction to start recording, the existing scanning protocol and a target scanning protocol for users to select. Doctors may select the target scanning protocol, and send an instruction to start the target scanning protocol via the human-machine interactive unit 70. The processor 20 may, in response to the instruction to start the target scanning protocol, control the ultrasonic probe to transmit the ultrasonic wave to the target tissue and receive the ultrasonic echo from the target tissue to acquire the ultrasonic echo signal, acquire the ultrasonic image according to the ultrasonic echo signal, and display the scanning interface corresponding to a first to-be-examined target section of the target scanning protocol via the display for users to perform scanning operations. Users may move the ultrasonic probe based on the guidance of the first to-be-examined target section to scan to acquire the ultrasonic image of the to-be-examined target section. The processor 20 may display the name of the target scanning protocol and the name of the current to-be-examined target section via the display interface, as well as the body mark for doctors' reference. It may also automatically configure the examination mode as the target examination mode of the setting parameter (or the target examination mode may be prompted first and then be performed after doctors' confirmation), and automatically configure the image mode as the target image mode of the setting parameter (or the target image mode may be prompted first and then be performed after doctors' confirmation). When it is currently in the real-time scanning state, the image parameter may be automatically configured as a target image parameter level of the setting parameter corresponding to the real-time scanning state (or the target image parameter level may be prompted first and then be performed after doctors' confirmation); in such situation, there is no need for doctors to conduct configuration, instead, they may only need to hold the ultrasonic probe for scanning, which is very convenient. After scanning a clip of ultrasonic images, it may be frozen by the doctor; and the processor 20 may automatically set the image parameter as the target image parameter level of the setting parameter corresponding to the image frozen state (or the target image parameter level may be prompted first and then be performed after doctors' confirmation). The processor 20 may also prompt the doctor to choose one or more frames of ultrasonic images on the display interface according to the setting parameters. After the frame(s) is(are) selected by the doctor, the processor 20 may also directly display a comment item, a comment position, a measured parameter and a body mark on the display interface according to the setting parameter for the doctor to perform comment and measurement, and also providing guidance for the doctor. After the labeling operation is done, the doctor may save images, and may just choose images that need to be saved. The processor 20 may, according to the storage mode of the setting parameter (or the storage mode may be prompted first and then be performed after doctors' confirmation), automatically save the image(s) selected by the doctor in the format storage of the setting parameter into the storage position of the setting parameter (or the image format and storage position may be prompted first and then be performed after doctors' confirmation). Different to-be-examined target sections may be stored in various ways. The human-machine interactive unit may be set up in such a way that it enables the doctor to use the same image-storage button to perform different storage modes according to different target sections. Of course, the human-machine interactive unit may also be set up in another way, which allows the doctor to use different image-storage buttons to perform different storage modes. After that, image(s) may be unfrozen; and the processor 20 may, according to the starting sequence of the to-be-examined target section, start the scanning interface corresponding to a next to-be-examined target section, so that the doctor can perform scanning operation until part or all the to-be-examined target sections of the target scanning protocol have been reviewed to acquire the ultrasonic images of the sections that the doctor want. It can be seen that the scanning protocol in ultrasonic automatic workflow can be customized with the methods disclosed herein which lead to rapid and efficient creation.

In the above embodiments, recording may be initiated by triggering an icon that indicates the instruction to start recording by the doctor. Another embodiment in which the way entering recording is somewhat different from the above embodiments may be provided in the present disclosure. In the embodiment, the method for quick creating a scanning protocol may include the following steps:

Step 1': the processor 20 receiving an instruction to start ultrasonic automatic workflow, and in response to the instruction to start ultrasonic automatic workflow, displaying at least one scanning protocol on the display interface of the display for a user to select. The scanning protocol may be an existing scanning protocol, or a template scanning protocol that can also guide the doctor to conduct the steps shown in FIG. 3. After a scanning protocol is selected by the doctor, the processor 20 may, in response to the instruction for selecting a scanning protocol, control an ultrasonic probe to transmit an ultrasonic wave to a target tissue and receive an echo of the ultrasonic wave to acquire an ultrasonic echo signal; acquire an ultrasonic image based on the ultrasonic echo signal and display a scanning interface of the to-be-examined section of the scanning protocol on the display interface. In the aforesaid embodiments, the doctors may perform one or more scanning operations of the to-be-examined section by themselves from making things out of nothing to obtain one or more to-be-examined target sections and setting parameters thereof; however, in this embodiment, the doctors may perform one or more scanning operations of the to-be-examined section based on a scanning protocol selected from the existing scanning protocols provided by the ultrasonic imaging apparatus to acquire one or more to-be-examined target sections and setting parameters thereof. Except for this, there is not much difference therebetween; and related description may be understood by referring the above-mentioned embodiments, which will not be repeated here.

Step 2': in response to the instruction to start recording, recording a scanning operation performed by the user based on the scanning interface by the processor 20 to acquire at least one to-be-examined target section and a setting parameter of the at least one to-be-examined target section. This step is the same as step 2 in the above embodiments, which will not be repeated here.

Step 3': after receiving the instruction to start recording, generating a target scanning protocol containing the at least one to-be-examined target section and the setting parameter of the at least one to-be-examined target section by the processor 20. This step is the same as step 3 in the above embodiments, which will not be repeated here.

It can be seen that in the present disclosure an appropriate time may be chosen to record the doctors' operation and the section acquisition by taking the section as a unit to automatically generate an executable target scanning protocol, reducing the workload of user customization, and making it more conveniently and easy for users to use automatic workflow to standardize daily ultrasound examination.

The above embodiments provide a method for quickly creating a scanning protocol; and based on the similar principle thereof, a method for quickly modify a scanning protocol is also be provided in the present disclosure, which may include the following steps:

Step 1": the processor 20 receiving an instruction to start ultrasonic automatic workflow, and displaying at least one scanning protocol containing at least one to-be-examined section for a user to select in response to the instruction to start the ultrasonic automatic workflow, wherein the processor 20 may, in response to an instruction to select scanning protocol, display a scanning interface of the to-be-examined section of the scanning protocol;

Step 2": the processor 20, in response to an instruction to start recording, recording a scanning operation on the scanning interface performed by the user to acquire at least one to-be-examined section and a setting parameter of the at least one to-be-examined section; and Step 3": the processor 20, after receiving a stop-recording instruction, updating an original setting parameter of the scanning protocol according to the acquired setting parameter, thereby completing the modification of the scanning protocol. The specific process thereof can be described in the aforesaid embodiments of the method for creating a scanning protocol, which will not be repeated herein.

Those skilled in the art may understand that all or part of the functions related to the methods in the above embodiments may be realized by means of hardware or computer programs. In the context of realizing all of part of the functions in the above embodiments by means of a computer program, the program may be stored in a computer-readable storage medium (that may include read-only memory, random access memory, magnetic disk, optical disk, hard disk, etc.), and be executed by a computer to realize the aforesaid functions. For example, when such a program is stored in a memory of a device, all or part of the above functions may be achieved when the program in the memory is executed by a processor. In addition, in the context of realizing all of part of the functions in the above embodiments by means of a computer program, the program may also be stored in a storage medium (such as a server, another computer, magnetic disk, optical disk, flash disk or portable hard disk) and then downloaded or copied to a memory of a local device, or the version of the program for the local device may be updated, all or part of the above functions may be achieved when the program in the storage medium is executed by a processor.

The present disclosure is illustrated with reference to various exemplary embodiments. However, those skilled in the art may recognize that the exemplary embodiments can be changed and modified without departing from the scope of the present disclosure. For example, various operation steps and components used to execute the operation steps may be implemented in different ways (for example, one or more steps may be deleted, modified, or combined into other steps) according to specific application(s) or any number of cost functions associated with the operation of the system.

In addition, as understood by those skilled in the art, the principles herein may be reflected in a computer program product on a computer-readable storage medium that is preloaded with computer-readable program code. Any tangible, non-temporary computer-readable storage medium can be used, including magnetic storage devices (hard disks, floppy disks, etc.), optical storage devices (CD-ROMs, DVDs, Blu Ray disks, etc.), flash memory and/or the like. The computer program instructions may be loaded onto a general purpose computer, a special purpose computer, or other programmable data processing device to form a machine, so that these instructions executed on a computer or other programmable data processing device can form a device that realizes a specified function. These computer program instructions may also be stored in a computer-readable memory that can instruct a computer or other programmable data processing device to run in a specific way, so that the instructions stored in the computer-readable memory can form a manufacturing product, including a realization device to achieve a specified function. The computer program instructions may also be loaded onto a computer or other programmable data processing device to execute a series of operating steps on the computer or other programmable device to produce a computer-implemented process, so that instructions executed on the computer or other programmable device can provide steps for implementing a specified function.

Although the principles herein have been shown in various embodiments, many modifications to structures, arrangements, proportions, elements, materials, and components that are specifically adapted to specific environmental and operational requirements may be used without deviating from the principles and scope of the present disclosure. These and other modifications and amendments will be included in the scope of the present disclosure.

The foregoing specific description has been illustrated with reference to various embodiments. However, those skilled in the art will recognize that various modifications and changes can be made without departing from the scope of the present disclosure. Accordingly, the present disclosure is illustrative rather than restrictive, and all such modifications will be included in its scope. Similarly, there are solutions to these and other advantages and problems of the various embodiments as described above. However, the benefits, the advantages, solutions to problems, and any elements that can produce them or make them more explicit should not be interpreted as critical, required, or necessary one. The term "comprise" and any other variations thereof used herein are non-exclusive; accordingly, a process, method, article or device that includes a list of elements may include not only these elements, but also other elements that are not explicitly listed or are not part of said process, method, article or device. In addition, the term "coupling" and any other variations thereof as used herein may refer to physical, electrical, magnetic, optical, communication, functional, and/or any other connection.

Those skilled in the art will realize that many changes can be made to the details of the above embodiments without departing from the basic principles of the present disclosure. The scope of the present disclosure shall therefore be determined in accordance with the following claims.

The invention claimed is:

1. A method for creating a scanning protocol that comprises a plurality of to-be-examined sections and setting parameters thereof, performed by an ultrasonic imaging apparatus comprising an ultrasonic probe, a human-machine interactive unit and a processor, wherein the method comprises:

receiving, by the human-machine interactive unit, an instruction to start recording;

in response to the instruction to start recording, displaying, by the human-machine interactive unit, a scanning interface, recording, by the processor, a scanning operation performed by a user based on the scanning interface to acquire a plurality of to-be-examined target sections and a setting parameter of each of the plurality of to-be-examined target sections; and generating, by the processor, a target scanning protocol containing the plurality of to-be-examined target sections and the setting parameter of each of the plurality of to-be-examined target sections, wherein said recording the scanning operation performed by the user based on the scanning interface to acquire the plurality of to-be-examined target sections and the setting parameter of each of the plurality of to-be-examined target sections comprises:

acquiring, by the processor, the plurality of to-be-examined target sections;

prompting, by the processor, the user to set a starting sequence of each of the plurality of to-be-examined target sections on the displayed scanning interface; and determining, by the processor, the starting sequence of each of the plurality of to-be-examined target sections according to an input by the user, and taking, by the processor, the starting sequence of each of the plurality of to-be-examined target sections as the setting parameter of each of the plurality of to-be-examined target sections, wherein the method further comprises:

automatically starting, by the processor according to the starting sequence, the scanning interface corresponding to a next to-be-examined target section for performing the scanning operation when determining that examination and recording of a current to-be-examined target section is completed.

2. The method according to claim 1, wherein before receiving the instruction to start recording, the method further comprises:

receiving, by the human-machine interactive unit, an instruction to start ultrasonic automatic workflow; and in response to the instruction to start the ultrasonic automatic workflow, displaying, by the human-machine interactive unit, an icon for triggering the instruction to start recording and at least one existing scanning protocol for the user to select, the existing scanning protocol comprising at least one existing to-be-examined section.

3. The method according to claim 1, further comprising:

in response to an instruction to start the target scanning protocol, controlling, by the processor, the ultrasonic probe to transmit an ultrasonic wave to a target tissue and receive an ultrasonic echo from the target tissue to acquire an ultrasonic echo signal; and acquiring, by the processor, an ultrasonic image based on the ultrasonic echo signal, and displaying, by the human-machine interactive unit based on the starting sequence of each of the plurality of to-be-examined target sections, the scanning interface corresponding to each of the plurality of to-be-examined target sections for the user to perform the scanning operation.

4. The method according to claim 1, wherein the scanning operation comprises at least one of: image-scanning operation, image-freezing operation, frame-selecting operation, labeling operation, image-saving operation and image-unfreezing operation; and the labeling operation comprises at least one of: adding a body mark, commenting, and measuring.

5. The method according to claim 4, wherein said recording, by the processor, the scanning operation performed by the user based on the scanning interface to acquire the plurality of to-be-examined target sections and the setting parameter of each of the plurality of to-be-examined target sections further comprises:

acquiring, by the processor, the current to-be-examined target section; and recognizing, by the processor, the scanning operation performed by the user, and when the scanning operation performed by the user is recognized as a predetermined key operation, determining, by the processor, that the examination and recording of the current to-be-examined target section is completed and acquiring, by the processor, a setting parameter of the current to-be-examined target section based on a record of the scanning operation from the image-scanning operation to the predetermined key operation.

6. The method according to claim 4, wherein the scanning operation at least comprises the image-scanning operation; the image-scanning operation comprises at least one of an examination mode, an image mode and an image parameter level that are adopted during an ultrasonic imaging process; and said ultrasonic imaging process comprises controlling the ultrasonic probe to transmit an ultrasonic wave to a target tissue and receive an ultrasonic echo from the target tissue to acquire an ultrasonic echo signal, and acquiring an ultrasonic image based on the ultrasonic echo signal; and said recording, by the processor, the scanning operation performed by the user based on the scanning interface to acquire the plurality of to-be-examined target sections and the setting parameter of each of the plurality of to-be-examined target sections further comprises:

acquiring, by the processor, the current to-be-examined target section; and recording, by the processor, at least one of a target examination mode, a target image mode and a target image parameter level that are adopted in the image-scanning operation, and taking, by the processor, the at least one of the target examination mode, the target image mode and the target image parameter level as a setting parameter of the current to-be-examined target section.

7. The method according to claim 4, wherein the scanning operation at least comprises the frame-selecting operation and the labeling operation; and said recording, by the processor, the scanning operation performed by the user based on the scanning interface to acquire the plurality of to-be-examined target sections and the setting parameter of each of the plurality of to-be-examined target sections further comprises:

acquiring, by the processor, the current to-be-examined target section;

after acquiring, by the human-machine interactive unit, an ultrasonic image selected by the user in the frame-selecting operation, recording, by the processor, an added comment item or comment position and taking, by the processor, the added comment item or the comment position as a setting parameter of the current to-be-examined target section; and/or after acquiring, by the human-machine interactive unit, an ultrasonic image selected by the user in the frame-selecting operation, recording, by the processor, an added measuring parameter and taking, by the processor, the added measuring parameter as a setting parameter of the current to-be-examined target section; and/or after acquiring, by the human-machine interactive unit, an ultrasonic image selected by the user in the frame-selecting operation, recording, by the processor, an added body mark and taking, by the processor, the body mark as a setting parameter of the current to-be-examined target section.

8. The method according to claim 4, wherein the scanning operation at least comprises the image-saving operation; and said recording, by the processor, the scanning operation performed by the user based on the scanning interface to acquire the plurality of to-be-examined target sections and the setting parameter of each of the plurality of to-be-examined target sections further comprises:

acquiring, by the processor, the current to-be-examined target section;

after receiving, by the human-machine interactive unit, an instruction to save image, recording, by the processor, a storage mode selected by the user and taking, by the processor, the storage mode as a setting parameter of the current to-be-examined target section, the storage mode comprising storing a single frame of ultrasonic image from frozen ultrasonic image(s), forward-storing a clip of ultrasonic images, backward-storing a clip of ultrasonic images, or storing static ultrasonic image(s); and/or after receiving, by the human-machine interactive unit, an instruction to save image, recording, by the processor, a storage position of a saved ultrasonic image and taking, by the processor, the storage position as a setting parameter of the current to-be-examined target section; and/or after receiving, by the human-machine interactive unit, an instruction to save image, recording, by the processor, an image format of a saved ultrasonic image and taking, by the processor, the image format as a setting parameter of the current to-be-examined target section; and/or after receiving, by the human-machine interactive unit, an instruction to print image, recording, by the processor, a print setting and taking, by the processor, the print setting as a setting parameter of the current to-be-examined target section.

9. The method according to claim 4, wherein said recording, by the processor, the scanning operation performed by the user based on the scanning interface to acquire the plurality of to-be-examined target sections and the setting parameter of each of the plurality of to-be-examined target sections further comprises:

acquiring, by the processor, the current to-be-examined target section; and after receiving, by the human-machine interactive unit, an instruction to select guide image, taking, by the processor, the selected guide image as a setting parameter of the current to-be-examined target section; or, extracting, by the processor, an anatomical structure contour from an ultrasonic image acquired by the scanning operation, searching, by the processor, a guide image that is most similar to the anatomical structure contour from a plurality of pre-stored guide images, and taking, by the processor, the searched guide image as a setting parameter of the current to-be-examined target section.

10. The method according to claim 4, wherein the scanning operation at least comprises the image-unfreezing operation; and the method further comprises:

after receiving, by the human-machine interactive unit, an instruction to unfreeze image, judging whether an ultrasonic image has been saved in the current to-be-examined target section, and deleting, by the processor, a setting parameter obtained currently if no ultrasonic image has been saved in the current to-be-examined target section.

11. The method according to claim 1, wherein after receiving, by the human-machine interactive unit, the instruction to start recording, the method further comprises:

displaying, by the human-machine interactive unit, a progress of acquiring the plurality of to-be-examined target sections and the setting parameter of each of the plurality of to-be-examined target sections in the scanning operation on the displayed scanning interface.

12. The method according to claim 1, wherein after receiving, by the human-machine interactive unit, the instruction to start recording, the method further comprises:

acquiring, by the processor, the current to-be-examined target section;

prompting, by the processor, the user to set a name of the target scanning protocol on the displayed scanning interface and determining the name of the target scanning protocol according to an input by the user; or, taking, by the processor, a predetermined first name as the name of the target scanning protocol; and prompting, by the processor, the user to set a name of the to-be-examined target section on the displayed scanning interface, determining, by the processor, the name of the to-be-examined target section according to an input by the user, and taking, by the processor, the determined name of the to-be-examined target section as a setting parameter of the current to-be-examined target section; or, taking, by the processor, a predetermined second name as the name of the to-be-examined target section, and taking, by the processor, the predetermined second name as a setting parameter of the current to-be-examined target section.

13. The method according to claim 1, wherein after receiving, by the human-machine interactive unit, the instruction to start recording, the method further comprises:

copying, by the processor, a to-be-examined target section selected by the user based on a received instruction to copy so as to acquire another group of setting parameter(s) of said to-be-examined target section; and/or deleting, by the processor, a setting parameter of the to-be-examined target section selected by the user based on a received instruction to retake so as to re-acquire a setting parameter; and/or deleting, by the processor, the to-be-examined target section selected by the user based on a received instruction to delete, and updating the starting sequence of other to-be-examined target sections; and/or inserting, by the processor, a new to-be-examined target section based on a received instruction to forward-insert before a to-be-examined target section selected by the user; and/or inserting, by the processor, a new to-be-examined target section based on a received instruction to backward-insert after a to-be-examined target section selected by the user; and/or pausing, by the processor, a current recording based on a received instruction to pause recording; and continuing the current recording based on a received instruction to continue recording.

14. The method according to claim 1, wherein after generating the target scanning protocol, the method further comprises:

receiving, by the human-machine interactive unit, an instruction to combine, and combining, by the processor, two target scanning protocols selected by the user into one target scanning protocol based on a sequence of the two target scanning protocols selected by the user, the two target scanning protocols selected by the user being interrelated.

15. A method for creating a scanning protocol that comprises a plurality of to-be-examined sections and setting parameters thereof, performed by an ultrasonic imaging apparatus comprising an ultrasonic probe, a human-machine interactive unit and a processor, wherein the method comprises:

receiving, by the human-machine interactive unit, an instruction to start ultrasonic automatic workflow, and in response to the instruction to start ultrasonic automatic workflow, displaying, by the human-machine interactive unit, at least one scanning protocol for a user to select, the scanning protocol comprising a plurality of to-be-examined sections;

in response to an instruction to select scanning protocol, controlling, by the processor, the ultrasonic probe to transmit an ultrasonic wave to a target tissue and receive an ultrasonic echo from the target tissue to acquiring an ultrasonic echo signal;

acquiring, by the processor, an ultrasonic image based on the ultrasonic echo signal and displaying, by the human-machine interactive unit, a scanning interface of a to-be-examined section of the scanning protocol;

recording, by the processor, a scanning operation performed by the user based on the scanning interface in response to an instruction to start recording to acquire a plurality of to-be-examined target sections and a setting parameter of each of the plurality of to-be-examined target sections; and generating, by the processor, a target scanning protocol containing the plurality of to-be-examined target sections and the setting parameter of each of the plurality of to-be-examined target sections, wherein said recording the scanning operation performed by the user based on the scanning interface to acquire the plurality of to-be-examined target sections and the setting parameter of each of the plurality of to-be-examined target sections comprises:

acquiring, by the processor, the plurality of to-be-examined target sections;

prompting, by the processor, the user to set a starting sequence of each of the plurality of to-be-examined target sections on the displayed scanning interface; and determining, by the processor, the starting sequence of each of the plurality of to-be-examined target sections according to an input by the user, and taking, by the processor, the starting sequence of each of the plurality of to-be-examined target sections as the setting parameter of each of the plurality of to-be-examined target sections, wherein the method further comprises:

automatically starting, by the processor according to the starting sequence, the scanning interface corresponding to a next to-be-examined target section for performing the scanning operation when determining that examination and recording of a current to-be-examined target section is completed.

16. An ultrasonic imaging apparatus, comprising:

an ultrasonic probe configured for transmitting an ultrasonic wave to a region of interest within a biological tissue and receiving an echo of the ultrasonic wave;

a transmitting/receiving control circuit configured for controlling the ultrasonic probe to transmit the ultrasonic wave to the region of interest and receive the echo of the ultrasonic wave to acquire an ultrasonic echo signal;

a human-machine interactive unit configured for receiving an input by a user and outputting visualization information; and a processor configured for: acquiring an ultrasonic image based on the ultrasonic echo signal; receiving an instruction to start recording via the human-machine interactive unit; in response to the instruction to start recording, displaying a scanning interface via the human-machine interactive unit, recording a scanning operation performed by the user based on the scanning interface to acquire a plurality of to-be-examined target sections and a setting parameter of each of the plurality of to-be-examined target sections; and generating a target scanning protocol containing the plurality of to-be-examined target sections and the setting parameter of each of the plurality of to-be-examined target sections, wherein the processor is further configured for:

acquiring the plurality of to-be-examined target sections;

prompting the user to set a starting sequence of each of the plurality of to-be-examined target sections on the displayed scanning interface; determining the starting sequence of each of the plurality of to-be-examined target sections according to an input by the user; and taking the starting sequence of each of the plurality of to-be-examined target sections as the setting parameter of each of the plurality of to-be-examined target sections, wherein the processor is further configured for:

automatically starting, according to the starting sequence, the scanning interface corresponding to a next to-be-examined target section for performing the scanning operation when determining that examination and recording of a current to-be-examined target section is completed.

17. The ultrasonic imaging apparatus according to claim 16, wherein the scanning operation comprises at least one of: image-scanning operation, image-freezing operation, frame-selecting operation, labeling operation, image-saving operation and image-unfreezing operation; and the labeling operation comprises at least one of: adding a body mark, commenting, and measuring.

18. The ultrasonic imaging apparatus according to claim 16, wherein the processor is further configured for: after receiving the instruction to start recording, acquiring the current to-be-examined target section;

prompting the user to set a name of the target scanning protocol on the displayed scanning interface of the human-machine interactive unit and determining the name of the target scanning protocol according to an input by the user; or, taking a predetermined first name as a name of the target scanning protocol; and prompting the user to set a name of the to-be-examined target section on the displayed scanning interface of the human-machine interactive unit, determining the name of the to-be-examined target section according to an input by the user, and taking the determined name of the to-be-examined target section as a setting parameter of the current to-be-examined target section; or, taking a predetermined second name as the name of the to-be-examined target section, and taking the predetermined second name as a setting parameter of the current to-be-examined target section.

19. The ultrasonic imaging apparatus according to claim 16, wherein the processor is further configured for: after generating the target scanning protocol, receiving an instruction to combine via the human-machine interactive unit, and combining two target scanning protocols selected by the user into one target scanning protocol based on a sequence of the two target scanning protocols selected by the user, the two target scanning protocols selected by the user being interrelated.

* * * * *